(12) United States Patent
Lentz et al.

(10) Patent No.: US 12,186,058 B2
(45) Date of Patent: Jan. 7, 2025

(54) MULTI-SENSOR IN-REAL-TIME BLOOD LOSS MONITOR

(71) Applicant: Eir on the Side of Health, Simpsonville, SC (US)

(72) Inventors: Kacey Lentz, Simpsonville, SC (US); Sarah Forbes, Manlius, NY (US); Christine O'Brien, St. Louis, MO (US); Ashley Perry, El Dorado Hills, CA (US); Haley Thorn, Indianapolis, IN (US)

(73) Assignee: Eir on the Side of Health, Simpsonville, SC (US)

( * ) Notice: Subject to any disclaimer, the term of this patent is extended or adjusted under 35 U.S.C. 154(b) by 338 days.

(21) Appl. No.: 17/241,449

(22) Filed: Apr. 27, 2021

(65) Prior Publication Data
US 2021/0330196 A1    Oct. 28, 2021

Related U.S. Application Data

(60) Provisional application No. 63/016,412, filed on Apr. 28, 2020.

(51) Int. Cl.
*A61B 5/02* (2006.01)
*A61B 5/00* (2006.01)

(52) U.S. Cl.
CPC ........ *A61B 5/02042* (2013.01); *A61B 5/0075* (2013.01); *A61B 5/7405* (2013.01); *A61B 5/742* (2013.01); *A61B 5/746* (2013.01); *A61B 2562/02* (2013.01)

(58) Field of Classification Search
CPC . A61B 5/02042; A61B 5/0075; A61B 5/7405; A61B 5/742; A61B 5/746; A61B 2562/02; G01N 33/49; G01F 22/00; G01F 23/292
See application file for complete search history.

(56) References Cited

U.S. PATENT DOCUMENTS

| | | | |
|---|---|---|---|
| 2016/0334261 A1* | 11/2016 | Wilson, III | G01F 23/24 |
| 2018/0266870 A1* | 9/2018 | Lin | G01G 17/04 |
| 2019/0282141 A1* | 9/2019 | Causey, III | A61B 5/14546 |
| 2020/0155016 A1* | 5/2020 | Najafi | A61B 5/747 |

* cited by examiner

*Primary Examiner* — Devin B Henson
*Assistant Examiner* — Evelyn Grace Park
(74) *Attorney, Agent, or Firm* — Husch Blackwell LLP

(57) ABSTRACT

A multi-sensor blood loss monitor system is provided. Specifically, the blood loss monitor system can include a weight sensor, a volume sensor within an aspirator canister, and an integration device. Further, the blood loss monitor system can further be connected to a suction head adaptor. The weight sensor can be used to determine how many surgical wipes have been disposed, thereby estimating a volume of blood loss. In addition, the volume sensor can include a fluid level sensor and an optical spectroscopy sensor to determine an amount of blood in the aspirator container. The integration device can combine these data to display a total blood loss, as well as trigger an alarm when a blood loss level is exceeded.

17 Claims, 3 Drawing Sheets

MULTI-SENSOR IN-REAL-TIME BLOOD LOSS MONITOR

CROSS-REFERENCE TO RELATED APPLICATIONS

This application claims priority to U.S. Provisional Patent Application Ser. No. 63/016,412, filed on Apr. 28, 2020, entitled "MULTI-SENSOR IN-REAL-TIME BLOOD LOSS MONITOR", the entire disclosure of which is incorporated herein by reference.

BACKGROUND OF THE INVENTION

Cesarean deliveries account for 31.9% of all deliveries in the US. During the procedure, doctors cut through large blood vessels to open the wall of the uterus to gain access to the baby. Because of the large quantity of blood introduced into the surgical field, doctors use various blood collection tools including but not limited to suction devices and surgical sponges. These tools are typically used to clean the surgical site of blood and other fluids such as amniotic fluid and saline.

Surgical sponges are the only method to efficiently clean the surgical site because suction is better suited for eliminating pooled blood. Because there are multiple locations of pooled blood and thus blood collection, total blood loss is visually estimated by the doctor. Doctors have become reasonably accurate at this estimation. Nevertheless, the various methods of blood collection used during a procedure make it difficult to accurately know the true amount of blood loss during an operation.

One device on the market captures scans of surgical sponges via a smart phone's or smart tablet's camera. Through software of the phone or tablet, it can estimate the hemoglobin content of the sponge. Even though this technology is available, healthcare professionals prefer the existing "guess and check" method because of the device's cost and the time it takes to use. In an operating room, the time needed to snap a picture of a sponge is valuable and could be used instead to undertake other life-saving or beneficial actions. Thus, there is a need for a blood loss monitoring device that is both easy-to-use and efficient in estimating blood loss.

BRIEF SUMMARY OF THE INVENTION

This disclosure generally relates to a blood loss monitor. More specifically, this disclosure relates to a multi-sensor real-time blood loss monitor.

In an embodiment, a blood loss monitor can be a multi-sensor system that combines information about the blood collected in a suction canister as well as blood collected in surgical wipes. A weight sensor can be paired with a canister that collects blood from a suction attachment, while an optical spectroscopy device can be placed inside the canister to determine hemoglobin content of the liquid in the canister. The reading from the optical spectroscopy device and weight sensor can give accurate information about the total blood loss without impacting the flow of the procedure. The monitor can track such blood collection so that healthcare professionals can make real-time decisions during an operation if blood loss is too great.

BRIEF DESCRIPTION OF THE DRAWINGS

The accompanying drawing shows the entire multi-sensor monitor that will be implemented in operating rooms.

Figure 1:
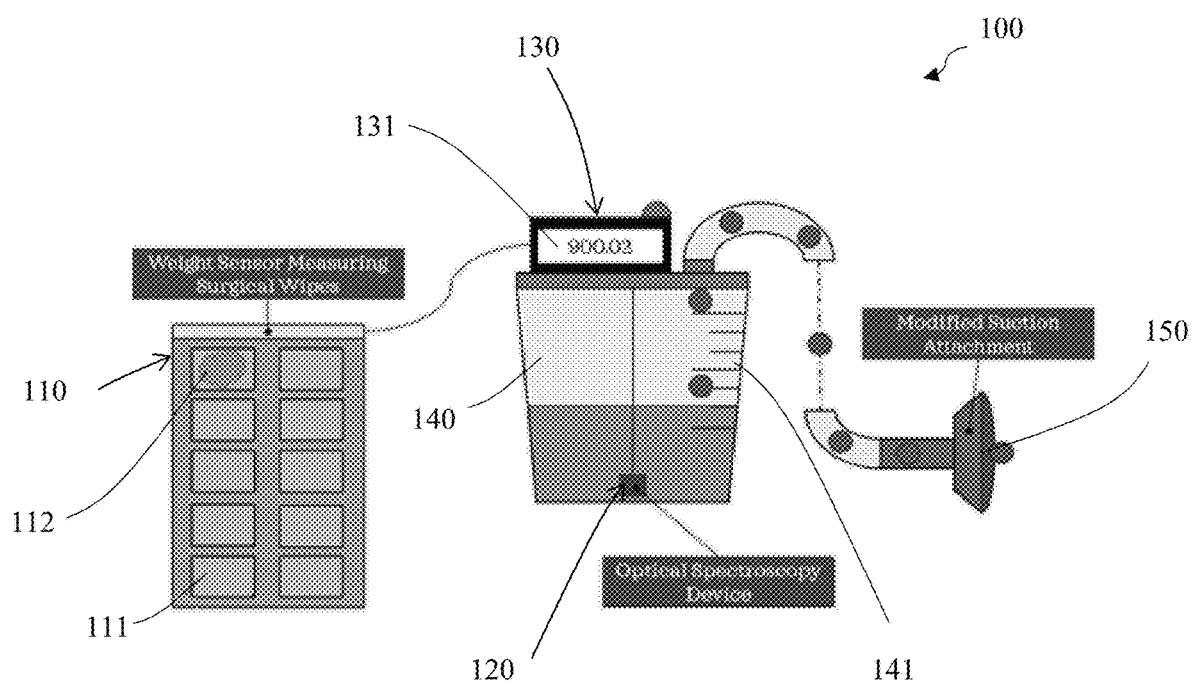
FIG. 1 illustrates a system diagram of a multi-sensor blood loss monitor according to an exemplary embodiment.

Before explaining the disclosed embodiment of the present invention in detail, it is to be understood that the invention is not limited in its application to the details of the particular arrangement shown, since the invention is capable of other embodiments. Exemplary embodiments are illustrated in referenced figures of the drawings. It is intended that the embodiments and figures disclosed herein are to be considered illustrative rather than limiting. Also, the terminology used herein is for the purpose of description and not of limitation.

DETAILED DESCRIPTION

While this invention is susceptible of embodiments in many different forms, there are shown in the drawings and will be described in detail herein specific embodiments with the understanding that the present disclosure is an exemplification of the principles of the invention. It is not intended to limit the invention to the specific illustrated embodiments. The features of the invention disclosed herein in the description, drawings, and claims can be significant, both individually and in any desired combinations, for the operation of the invention in its various embodiments. Features from one embodiment can be used in other embodiments of the invention.

Referring to FIG. 1, a system diagram of an exemplary multi-sensor blood loss monitor system 100 is illustrated. In general, the system 100 may include a weight sensor 110, a volume sensor 120, and an integration device 130. In an embodiment, the weight sensor 110 can be attached to existing hangers used for surgical wipe collection in operation suites. Currently, operating room procedure for saturated wipes is to put a number of wipes into a rack that contains a number of slots 111. The number of wipes (an example wipe 112 is illustrated) in each slot 111 may depend on the number of healthcare professionals working at that time.

In an embodiment, as described below, the volume sensor 120 can determine and analyze the volume of blood collected in an aspirator canister 140. The volume sensor 120 can instruct or otherwise work in conjunction with the canister 140 to eliminate saline and amniotic fluid volumes that are also collected in the aspirator canister 140.

The integration device 130 can synthesize information from both the weight sensor 110 and the optical spectroscopy sensor 120 and display the resulting blood loss volume on a display 131. The display 131 can be a screen built into the integration device 130 itself, or an external screen that the integration device 130 is configured to output to.

Data from both the weight sensor 110 and the volume sensor 120 can be combined into one number for a volume of blood loss in the patient at the time of the checking. By way of example, the volume of blood loss can be shown in milliliters or other suitable units. When a specific blood loss volume threshold, set prior to the procedure by a doctor or nurse, is reached, an indicator can be configured to alert nearby healthcare workers, particularly those involved in the procedure. Such an indicator can be visual, such as a light, or audio, such as an alarm, or other suitable indicators or a combination thereof.

In some embodiments, a suction head adaptor 150 can be used with the multi-sensor blood loss monitor system 100 to increase the amount of blood collected in the aspirator canister 140, which can be analyzed using the volume sensor 120. The suction head adaptor 150 can decrease the number of surgical wipes used for collection and increase the accuracy of blood loss volume measurement, as compared to measuring blood loss solely based on weight sensor measuring surgical wipes. Integrated use with the suction head adaptor 150 may allow for fluid collection during a procedure to be more centralized to the aspirator canister 140, thus allowing for a better estimate of blood and general fluid loss.

In practice, before a procedure, healthcare professionals may input a size of surgical laps and aspirator canisters that will be used. The volume sensor 120 can be placed inside existing aspirator canisters in operating rooms to determine blood loss volume within said canister. The volume sensor 120 can take in a blood volume from the aspirator canister 140 using many different types of setups and sensors. Moreover, a volume indicator strip 141 can be used to determine the volume of fluid collected in the aspirator canister 140.

Figure 2:
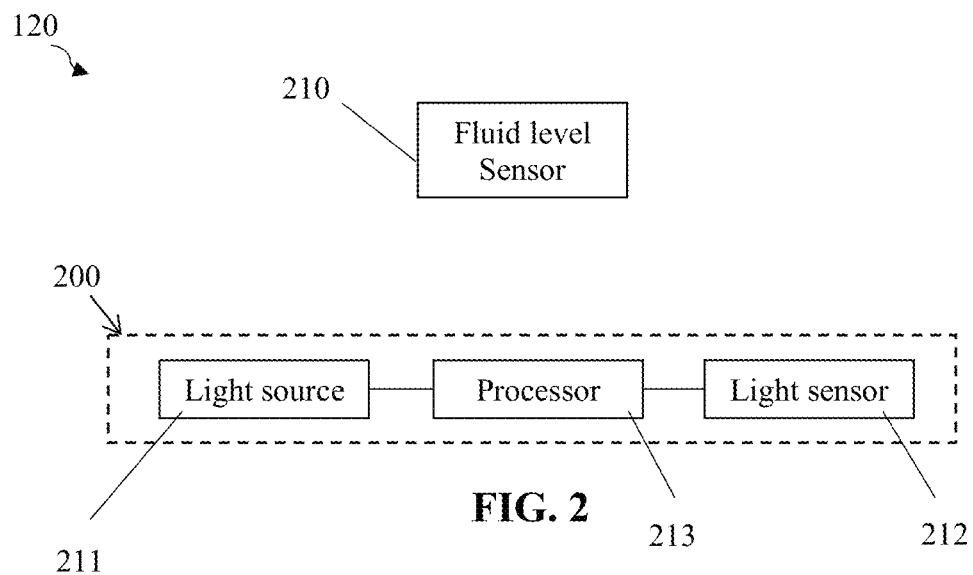
FIG. 2 illustrates a volume sensor for used in the multi-sensor blood loss monitor according to the exemplary embodiment.
Figure 3:
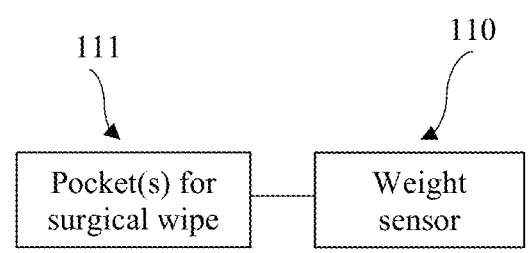
FIG. 3 illustrates a weight sensor for used in the multi-sensor blood loss monitor according to the exemplary embodiment.

Turning to FIG. 2, in one embodiment, the volume sensor 120 can be a fluid level sensor 210. In this configuration, a button can be included on the integration device 130 that can be pushed to indicate that amniotic fluid has been introduced in the system. This system can account for a set volume of approximately one hundred twenty milliliters (120 mL), which is accepted by many doctors as an accurate approximation of the amount of fluid in an amniotic sack, as being in the total fluid volume. Thus, in some embodiments the amniotic fluid volume may be omitted from the total blood loss volume estimate.

The volume sensor 120 can also include an optical spectroscopy setup as shown in FIG. 2, an optical spectroscopy sensor 200 can be used alongside the fluid level sensor 210 to determine what percentage of the fluid is blood. The optical spectroscopy sensor 200 can include a light source 211 that emits at minimum infrared or near-infrared light, at least one light sensor 212 to detect the amount of light that is transmitted through the fluid and/or reflected by the fluid, and a processor 213 that analyzes the signals arising from the light source and sensor. A specific wavelength for hemoglobin, which falls in the near-infrared to infrared range, can be included, but wavelengths for other fluids that may be introduced to the aspirator canister 140 during suctioning may also be included (e.g., green for meconium). Different wavelengths help ensure that data being reported by the optical spectroscopy sensor 200 is the hemoglobin content rather than hemoglobin with saline, meconium, etc. By multiplying the percent by volume of blood in the aspirator canister 140 and the total fluid volume collected in the aspirator canister 140, the blood loss volume in the aspirator canister 140 can be estimated. In this configuration, the volume sensor can estimate the blood loss volume itself, or the data can be transmitted to the integration device 130 for calculation.

The weight sensor 110 can make use of known (or foreseeable) technology and procedures that are already common in operating rooms, such as existing surgical wipe accounting racks. Each time a surgical wipe is placed into a slot (also referred to as a pocket) 111 on the weight sensor 110, a weight increase occurs. The pocket 111 can take the shape of a tray, a container, or other suitable means for collecting surgical wipes. If this weight increase is within a weight range predetermined as corresponding to a surgical wipe being added to the accounting drape and is sustained for 5 seconds, the weight sensor 110 can automatically add in the total weight change. The weight sensor 110 can also subtract the original weight of the wipe which can give a rough approximation of the weight of blood/fluid in a particular surgical wipe. This weight can then be converted to a volume in suitable units such as milliliters (using known or foreseeable methods) that can be added to the total blood loss volume estimate from the overall multi-sensor blood loss monitor system 100.

In some embodiments, a vibration detection sensor can be used in lieu of or in addition to the weight sensor 110. In this case, a movement of the accounting rack that corresponds to a specific voltage range can be used to detect when a surgical wipe is added to the rack. Each time this occurs, an average volume of fluid contained in a surgical lap of the size being used can be added to the total blood loss volume. The size of the laps being used can be input into the integration device 130 prior to the procedure.

Figure 4:
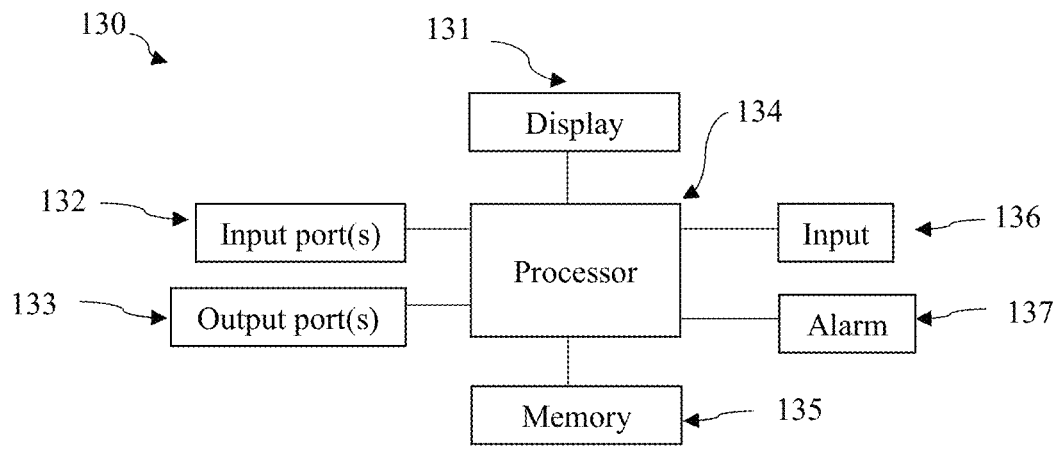
FIG. 4 illustrates an integration device for used in the multi-sensor blood loss monitor according to the exemplary embodiment.

Referring to FIG. 4, the integration device 130 can comprise one or more input ports 132 to receive inputs from the weight sensor 110 on the racks and the volume sensor 120 in the aspirator canister 140. Moreover, the integration device 130 can comprise the display 131. The display 131 can be one or more seven-segment display, LED, LCD, or other suitable displays. Alternatively, or additionally, the integration device 130 can also comprise one or more output ports 133 to be connected to an external display not built-in to the integration device 130.

The integration device 130 can further include a processor 134 and a memory 135. When executing programming stored on the memory 135, the processor 134 can convert information obtained from connected sensors into a volume (such as in a unit of milliliter) that is then displayed on the display 131.

Prior to a procedure, healthcare professionals can set a threshold limit to when they want the system to react. By way of example, in an embodiment, the threshold limit can be between 400 mL and 1000 mL at 100 mL increments. This threshold limit can be set by an input device 136, such as a keyboard or a keypad, connected to the integration device 130. Alternatively, or additionally, the integration device 130 can also comprise one or more input mechanisms such as a knob, a lever, a keypad, a touchscreen, or other suitable means used for inputs 136.

At the abovementioned threshold, a visual and/or an auditory alarm 137 can be triggered, such as an indicator light on top changing from green to red and/or an accompanying audible alarm. Certainly, other suitable alarms can also be used. Such alarm 137 can indicate that the patient has lost too much blood and intervention in the form of medications, fluids, transfusions, etc. should be administered. The alarm 137 can be built-in to the integration device 130, or it can be external and connected to the integration device 130.

As set forth above, the multi-sensor blood loss monitor system 100 can be used in conjunction with current technology in operating rooms—nurses can read the number off a display built into the integration device 130 or the multi-sensor blood loss monitor system 100 can be connect to existing monitors, so blood loss volume can be tracked similarly to how blood pressure or heart rate are tracked.

Figure 5:
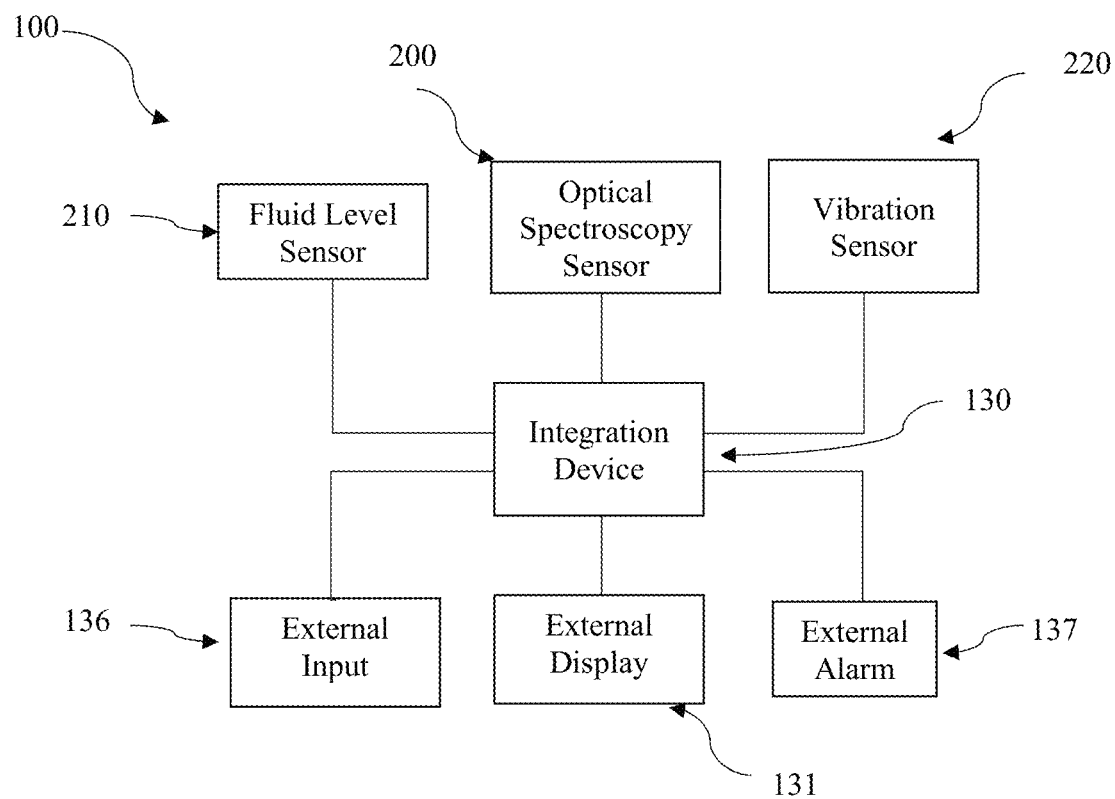
FIG. 5 illustrates a more detailed system diagram system diagram of a multi-sensor blood loss monitor according to another exemplary embodiment.

FIG. 5 illustrates an exemplary embodiment of the multi-sensor blood loss monitor system 100 with various sensor integration. As explained above, a fluid level sensor 210 can be used to determine the total volume of fluid in the aspirator canister 140. The type of the aspirator canister 140 being used would be known and thus by knowing the level of fluid in the aspirator canister 140, the percentage of the aspirator canister 140 that is filled can be calculated. Multiplying this percentage by the total volume of the aspirator canister 140 may result in the total volume of fluids in the aspirator canister 140. In certain embodiments, the fluid level sensor 210 can be omitted if there are other methods for determining the volume in the aspirator canister 140.

The optical spectroscopy sensor 200 (such as an infrared proximity sensor or other light or near-infrared detector) can be used to measure light reflected from the contents of the canister. Generally, blood falls in the near infrared spectrum—by measuring the light reflected, the percentage of blood within the collected fluids can be calculated. The percentage multiplied by the volume found using the level of the fluids in the aspirator canister 140 determined by the fluid level sensor 210 can then determines the volume of blood in the aspirator canister 140.

In this embodiment, a vibration sensor (such as a piezo vibration sensor) 220 can be used to detect touch/vibrations from a surgical wipe being placed into counting bags in the operating room. When the sensor 220 moves back and forth, a certain voltage can be created by a voltage comparator inside of the vibration sensor, and if the voltage exceeds a certain threshold, a single lap could be accounted for in the final blood volume. With this particular setup, the addition of a lap would instruct the multi-sensor blood loss monitor system 100 to add a predetermined blood volume estimate for a given size of surgical wipes to the final blood loss volume. As explained above, in lieu of the vibration sensor, the weight sensor 110 can also be used so long as there is a way to determine when a surgical wipe is added to the bag and a method for knowing or approximating the weight of said surgical wipe.

The integration device 130 can be used to analyze the inputs from the various sensors and inputs to return the total blood loss volume and display this volume. The integration device 130 provides for a way to compile and integrate information collected from the various sensors and inputs and outputting usable information in the form of the final blood loss volume and signals for thresholds of this volume being met.

An input 136 connected to a device (such as a mini pushbutton switch or a keypad) can be used to make selections such as blood volume thresholds for the system. Likewise, other types of input can also be used so long as there is a way for inputting decisions made by physicians that effect calculations and alarms. As explained above, the input device can be built-in to the integration device 130, or an external input connected to the multi-sensor blood loss monitor system 100.

Likewise, a display (such as a segment display) can be used to display the total blood loss volume in milliliters. Again, the display can be built-in to the integration device 130 or can be an external display connected to the multi-sensor blood loss monitor system 100. Moreover, alarms (such as RGB LEDs or other audio or visual indicators) can be used to alert when the blood loss threshold has been reached.

From the foregoing, it will be seen that this invention is one well adapted to attain all the ends and objects hereinabove set forth together with other advantages which are obvious, and which are inherent to the structure. It will be understood that certain features and sub combinations are of utility and may be employed without reference to other features and sub combinations. This is contemplated by and is within the scope of the claims. Since many possible embodiments of the invention may be made without departing from the scope; thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A blood loss monitor system comprising:
   a volume sensor coupled to an integration device, the volume sensor configured to gather a first data regarding a first volume of blood loss within a canister;
   a second sensor coupled to the integration device, the second sensor configured to gather a second data regarding a second volume of blood loss;
   an optical spectroscopy sensor coupled to the integration device, the optical spectroscopy sensor configured to gather a third data including a percentage of fluid being blood;
   wherein the optical spectroscopy sensor comprises a light source, a light sensor, and a processor, and wherein the processor is configured to analyze signals collected from each of the light source and the light sensor and is configured to calculate the percentage of the fluid being blood;
   wherein the second sensor is a vibration sensor, and the second volume of blood loss is based on a number of surgical wipes that have been disposed of; and
   wherein the integration device is configured to calculate a total blood loss.

2. The blood loss monitor system of claim 1, wherein the integration device is configured to calculate the total blood loss based on the first volume of blood loss and the second volume of blood loss.

3. The blood loss monitor system of claim 1, wherein the second sensor is a weight sensor and the second volume of blood loss is based on a weight of surgical wipes disposed.

4. The blood loss monitor system of claim 1, wherein in response to the total blood loss exceeding a threshold, the integration device is further configured to trigger an alarm.

5. The blood loss monitor system of claim 4, wherein the alarm is a visual indicator built-in to the integration device.

6. The blood loss monitor system of claim 4, wherein the alarm is an audio indicator built-in to the integration device.

7. The blood loss monitor system of claim 4, wherein the alarm is an external indicator coupled to the integration device.

8. The blood loss monitor system of claim 1, further comprising a display coupled to the integration device, wherein the integration device is further configured to show the total blood loss on the display.

9. The blood loss monitor system of claim 1, wherein the integration device further comprises a display, and the integration device is further configured to show the total blood loss on the display.

10. The blood loss monitor system of claim 1, wherein the volume sensor is a fluid level sensor placed within the canister, wherein the fluid level sensor is configured to determine the first volume of blood loss by measuring a fluid level within the canister.

11. The blood loss monitor system of claim 1, the volume sensor further comprises a fluid level sensor
configured to measure a level of a fluid within the canister.

12. The blood loss monitor system of claim 1, wherein the blood loss monitor system further comprises a suction head adaptor configured to collect fluid into the canister.

13. A blood loss monitor comprising:
a volume sensor coupled to a processor, the volume sensor configured to gather a first data regarding a first volume of blood loss within a canister;
a second sensor coupled to the processor, the second sensor configured to gather a second data regarding a second volume of blood loss;
an optical spectroscopy sensor coupled to the processor, the optical spectroscopy sensor configured to gather a third data including a percentage of fluid being blood;
wherein the optical spectroscopy sensor comprises a light source and a light sensor, and wherein the processor is configured to analyze signals collected from each of the light source and the light sensor and is configured to calculate the percentage of the fluid being blood;
wherein the second sensor is a vibration sensor, and wherein the second data includes a number of surgical wipes that have been disposed;
the processor is configured to calculate a total blood loss based on the first data and the second data.

14. The blood loss monitor of claim 13, wherein in response to the total blood loss exceeding a threshold, the processor is further configured to trigger an alarm.

15. The blood loss monitor of claim 13, wherein the volume sensor is a fluid level sensor placed within the canister, and wherein the first data includes a fluid level within the canister.

16. The blood loss monitor of claim 13 further comprising:
a display coupled to the processor, the processor further configured to show the total blood loss on the display; and
an alarm coupled to the processor, wherein in response to the total blood loss exceeding a threshold, the integration device is further configured to trigger the alarm.

17. A blood loss monitor system comprising:
a fluid level sensor placed within a canister and coupled to an integration device, the fluid level sensor configured to gather a first data including a level of a fluid within the canister;
an optical spectroscopy sensor coupled to the integration device, the optical spectroscopy sensor configured to gather a second data including a percentage of the fluid being blood;
a third sensor coupled to the integration device, the third sensor configured to gather a third data regarding including an amount of surgical wipes disposed;
wherein the optical spectroscopy sensor comprises a light source, a light sensor, and a processor, and wherein the processor is configured to analyze signals collected from each of the light source and the light sensor and is configured to calculate the percentage of the fluid being blood;
the integration device further coupled to a display and an alarm, the integration device being configured to:
calculate a total blood loss based on the first data, the second data, and the third data;
show the total blood loss on the display; and
trigger the alarm in response to the total blood loss exceeding a threshold.

* * * * *